United States Patent
Ichikawa (10) Patent No.: US 7,445,336 B2
(45) Date of Patent: Nov. 4, 2008

(54) FUNDUS CAMERA

(75) Inventor: Naoki Ichikawa, Gamagori (JP)

(73) Assignee: Nidek Co., Ltd., Gamagori (JP)

( * ) Notice: Subject to any disclaimer, the term of this patent is extended or adjusted under 35 U.S.C. 154(b) by 363 days.

(21) Appl. No.: 11/254,730

(22) Filed: Oct. 21, 2005

(65) Prior Publication Data

US 2007/0013867 A1    Jan. 18, 2007

(30) Foreign Application Priority Data

Oct. 21, 2004   (JP)   .............. 2004-307506
Oct. 21, 2004   (JP)   .............. 2004-307507

(51) Int. Cl.
    *A61B 3/14* (2006.01)
(52) U.S. Cl. ................... 351/206; 351/208
(58) Field of Classification Search ......... 351/206–208, 351/214, 216–218
    See application file for complete search history.

(56) References Cited

U.S. PATENT DOCUMENTS

| 5,463,430 A |  | 10/1995 | Isogai et al. | ............... 351/208 |
| 7,275,824 B2 | * | 10/2007 | Hoshino | ..................... 351/206 |
| 2005/0068496 A1 |  | 3/2005 | Ichikawa | ..................... 351/206 |
| 2005/0117115 A1 |  | 6/2005 | Ichikawa | ..................... 351/206 |

FOREIGN PATENT DOCUMENTS

| JP | A 5-95907 | 4/1993 |
| JP | A 7-88082 | 4/1995 |
| JP | A 8-275921 | 10/1996 |
| JP | A 2000-5131 | 1/2000 |
| JP | A 2001-346764 | 12/2001 |
| JP | A 2003-88503 | 3/2003 |
| JP | A 2003-245253 | 9/2003 |

* cited by examiner

*Primary Examiner*—Mohammed Hasan
(74) *Attorney, Agent, or Firm*—Oliff & Berridge, PLC (57) ABSTRACT

A fundus camera, in which operability is improved while not impairing the convenience of the function of automatic alignment, has a photographing part including a fundus photographing optical system, a moving unit which moves the photographing part, an observation optical system having a first image-pickup element which picks up a fundus image, an observation optical system having a second image-pickup element which picks up an anterior-segment image, a display unit capable of displaying the images, a control part which obtains information on alignment of the photographing part with the eye and controls driving of the moving unit based on the alignment information so that an alignment state satisfies a first reference condition, and a first input switch for inputting a signal for display switching from the fundus image to the anterior-segment image, wherein the control part prohibits the driving of the moving unit when the signal is inputted.

10 Claims, 5 Drawing Sheets

FIG. 7

FUNDUS CAMERA

BACKGROUND OF THE INVENTION

1. Field of the Invention

The present invention relates to a fundus camera for photographing a fundus of an eye of an examinee.

2. Description of Related Art

Conventionally, in fundus photographing using a fundus camera, rough alignment of a photographing part with an eye of an examinee is firstly performed while an image of an anterior-segment of the eye displayed on a monitor is observed, and then fine alignment of the photographing part with a fundus portion to be photographed is performed while an image of a fundus of the eye displayed on the monitor through display switching is observed. In recent years, a fundus camera having the function of automatically performing such alignment has been proposed (see Japanese Patent Application Unexamined Publication No. Hei8-275921 for example).

Incidentally, in a fundus camera of non-mydriasis type utilizing natural mydriasis of the eye, fixation of the eye tends to be unstable since brightness of a fixation lamp for fixing a visual line of the examinee (the eye of the examinee) is suppressed to such an extent that a pupil of the eye does not contract.

In the fundus camera having the function of the automatic alignment, even in the case of the eye of which fixation is unstable, alignment can be performed so as to bring about a state where display switching from the anterior-segment image to the fundus image becomes possible at the time when the fixation is temporarily stabilized. However, the fixation of the eye frequently becomes unstable again also after the display switching from the anterior-segment image to the fundus image. In such cases, for making a check of stability of the fixation and the like, it is sometimes more preferable to make display switching from the fundus image to the anterior-segment image. Alternatively, it is sometimes more preferable to perform switching from a mode for automatic alignment to a mode for manual alignment. In such cases, it is desirable to decrease the number of operations of switches and the like as much as possible.

SUMMARY OF THE INVENTION

An object of the invention is to over come the problems described above and to provide a fundus camera in which operability is improved while not impairing the convenience of the function of automatic alignment.

To achieve the objects and in accordance with the purpose of the present invention, a fundus camera has a photographing part in which a fundus photographing optical system is arranged, a moving unit which moves the photographing part, a fundus observation optical system having a first image-pickup element which picks up an image of the fundus, an anterior-segment observation optical system having a second image-pickup element which picks up an image of an anterior-segment of the eye, a display unit capable of displaying the fundus image picked up by the first image-pickup element and the anterior-segment image picked up by the second image-pickup element, a control part which obtains information on alignment of the photographing part with the eye and controls driving of the moving unit based on the obtained alignment information so that an alignment state of the photographing part with the eye satisfies a first reference condition, and a first input switch for inputting a signal for switching a display on the display unit from the fundus image to the anterior-segment image, wherein the control part prohibits the driving of the moving unit when the signal from the first input switch is inputted.

Additional objects and advantages of the invention are set forth in the description which follows, are obvious from the description, or may be learned by practicing the invention. The objects and advantages of the invention may be realized and attained by the fundus camera in the claims.

BRIEF DESCRIPTION OF THE DRAWINGS

The accompanying drawings, which are incorporated in and constitute a part of this specification, illustrate embodiments of the present invention and, together with the description, serve to explain the objects, advantages and principles of the invention. In the drawings.

DETAILED DESCRIPTION OF THE PREFERRED EMBODIMENTS

Figure 1:
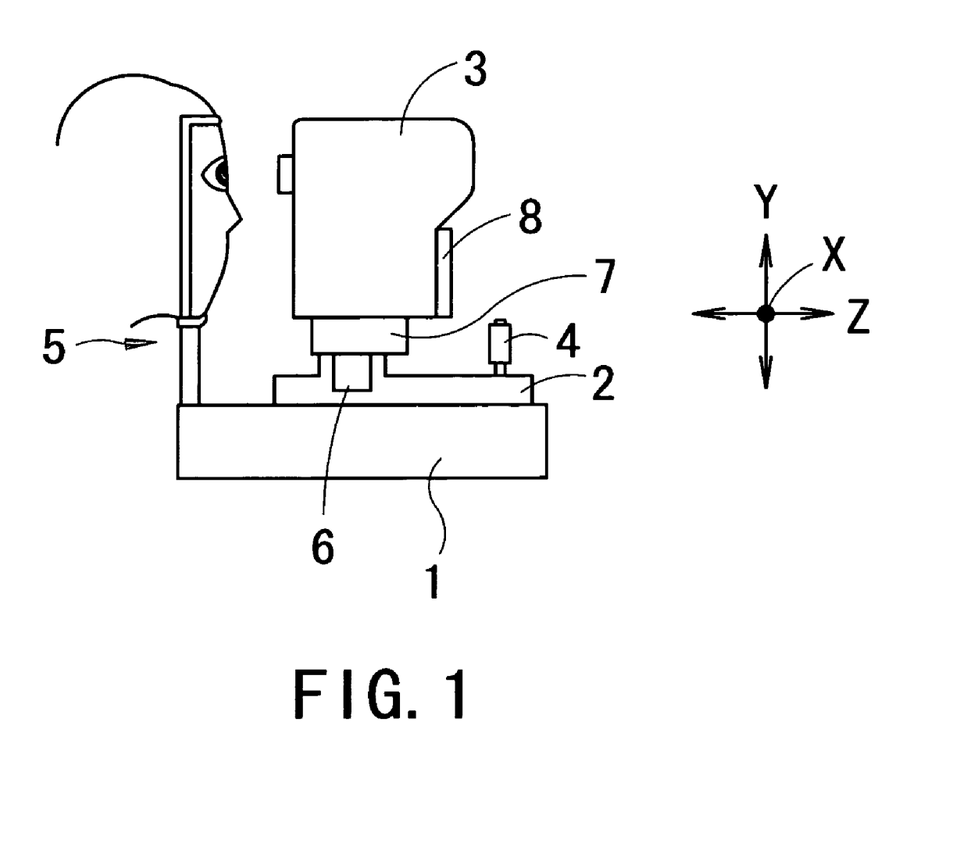
FIG. 1 is a view showing a schematic configuration of a fundus camera of non-mydriasis type consistent with one embodiment of the present invention.

A detailed description of one preferred embodiment of a fundus camera embodied by the present invention is provided below with reference to the accompanying drawings. FIG. 1 is a view showing a schematic configuration of a fundus camera of non-mydriasis type consistent with the preferred embodiment of the present invention.

The fundus camera includes a base 1, a moving base 2 movable in a right-and-left direction (hereinafter referred to as an "X-direction") and a back-and-forth direction (hereinafter referred to as a "Z-direction") with reference to the base 1 through tilting operation of a joystick 4, a photographing part 3 movable in the right-and-left direction, an up-and-down direction (hereinafter referred to as a "Y-direction") and the back-and-forth direction with reference to the moving base 2 under control of a control part 81 to be described later, and a face supporting unit 5 fixedly arranged on the base 1 for supporting a face (head) of an examinee. In an X- and Z-moving unit 7, a Z table movable in the Z-direction is arranged on a Y table, an X table movable in the X-direction is arranged on the Z table, and the photographing part 3 is arranged on the X table. The X- and Z-moving unit 7 moves the Z and X tables by their respective moving mechanisms consisting of a motor and the like to move the photographing part 3 in the X- and Z-directions. A Y-moving unit 6 moves the Y table by its moving mechanism consisting of a motor and the like to move the photographing part 3 in the Y-direction. Besides, for this kind of three-dimensional moving mechanism, a known mechanism may be employed. In addition, the photographing part 3 is moved in the Y-direction also by actuating the Y-moving unit 6 through rotary operation of the joystick 4. A monitor 8 for displaying an observation image and a photographed image is provided on an examiner's part of the photographing part 3.

Figure 2:
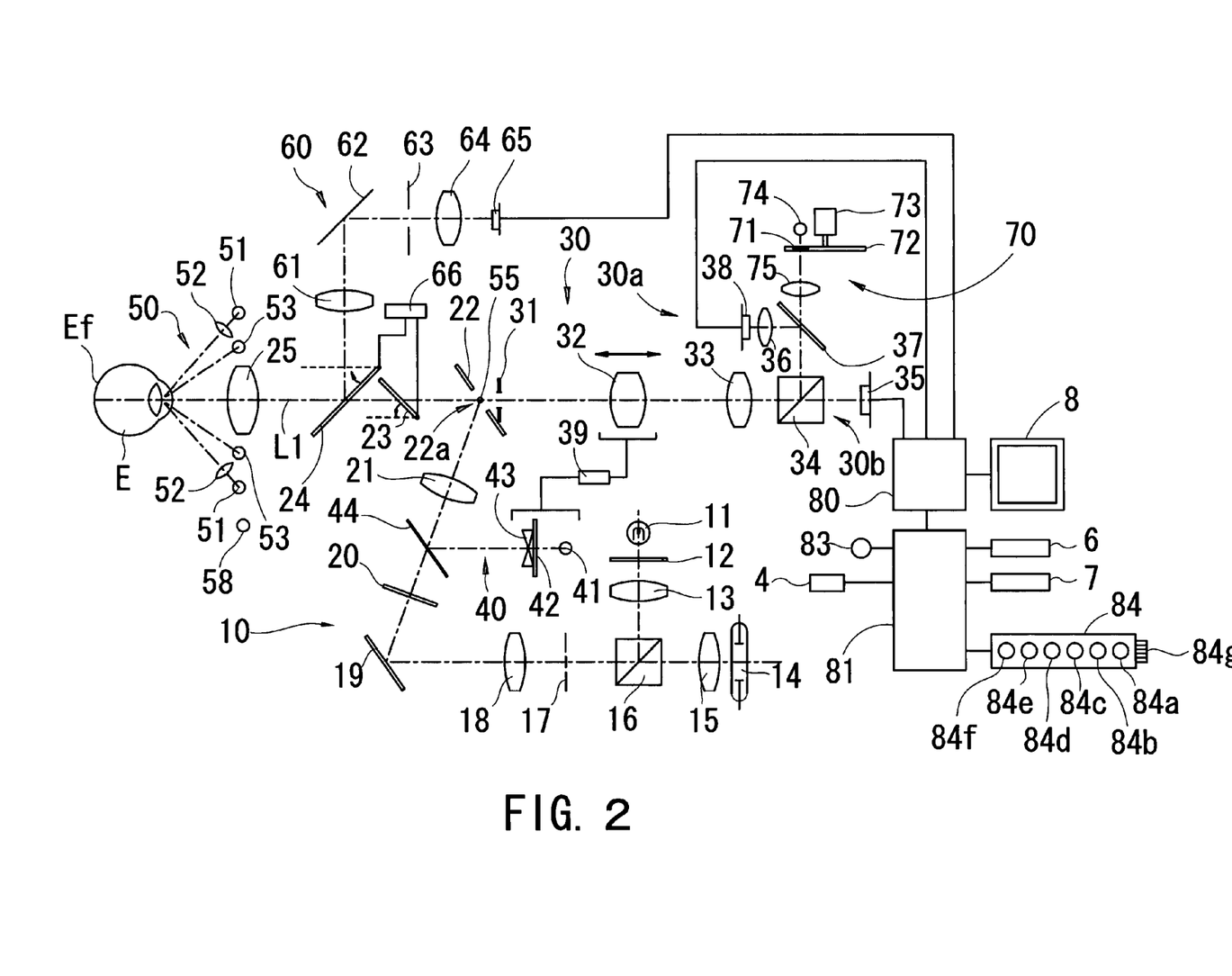
FIG. 2 is a view showing a schematic configuration of an optical system and a control system of the fundus camera.

FIG. 2 is a view showing a schematic configuration of an optical system and a control system housed in the photographing part 3. The optical system includes an illumination optical system 10, a fundus observation/photographing optical system 30, a focus target projection optical system 40, an alignment target projection optical system 50, an anterior-segment observation optical system 60, and a fixation target presenting optical system 70.

<Illumination Optical System 10>

The illumination optical system 10 includes an illumination optical system for fundus observation and an illumination optical system for photographing. Illumination light emitted from an illumination light source 11 for fundus observation such as a halogen light is made into infrared illumination light by an infrared transmission filter 12 which transmits light within an infrared wavelength range of approximately 750 nm to approximately 880 nm, and reflected by a diachronic mirror 16 via a condenser lens 13. The diachronic mirror 16 has a wavelength-selecting property of reflecting approximately all light within an infrared wavelength range and transmitting approximately all light within a visible wavelength range. The infrared illumination light reflected by the diachronic mirror 16 passes through a slit plate 17, a relay lens 18, a total reflection mirror 19, a black dot plate 20 having a black dot at its center, a half mirror 44 and a relay lens 21, and is reflected by an aperture mirror 22 to be projected onto a fundus Ef of an eye E of the examinee via an objective lens 25. The slit plate 17 has a ring-slit aperture. Besides, an infrared light source such as an infrared light-emitting diode may be used instead of the light source 11 such as a halogen light and the filter 12.

Visible illumination light emitted from a visible illumination light source 14 for photographing such as a flash light passes through a condenser lens 15 and is transmitted through the diachronic mirror 16 to be projected onto the fundus Ef via the slit plate 17 to the objective lens 25.

<Fundus Observation/Photographing Optical System 30>

The fundus observation/photographing optical system 30 includes a fundus observation optical system 30a and a photographing optical system 30b. The infrared light and the visible light reflected from the fundus Ef pass through the objective lens 25, an aperture 22a in the aperture mirror 22, a photographing diaphragm 31 arranged in the vicinity of the aperture 22a, a focusing lens 32 and an image forming lens 33 to enter a diachronic mirror 34. The photographing diaphragm 31 is arranged in a position approximately conjugate with a pupil of the eye E with reference to the objective lens 25. The focusing lens 32 is arranged movably by a moving mechanism 39 consisting of a motor and the like, in a direction of an optical axis L1 of the fundus observation/photographing optical system 30 (i.e., an optical axis of the objective lens 25). The diachronic mirror 34 has a wavelength-selecting property of reflecting approximately all light within the infrared wavelength range, and reflecting a part (a small proportion) of light within the visible wavelength range and transmits the other part (a large proportion). The visible reflection light transmitted through the diachronic mirror 34 is photo-received on a CCD camera 35 for photographing having sensitivity to the visible wavelength range to form an image of the fundus Ef. Also, the infrared reflection light reflected by the diachronic mirror 34 is reflected by a diachronic mirror 37 to pass through a relay lens 36, and photo-received on a CCD camera 38 for fundus observation having sensitivity to the infrared wavelength range to form an image of the fundus Ef. The diachronic mirror 37 has a wavelength-selecting property of reflecting approximately all light within the infrared wavelength range, and transmitting approximately all light within the visible wavelength range. Besides, the CCD camera 38 doubles as image-pickup means for focus target detection to be described later (i.e., the fundus observation optical system 30a doubles as a focus target detection optical system), and picks up the image of the fundus Ef formed by the light source 11 and images of focus targets formed by the focus target projection optical system 40 to be described later. Besides, it is advantageous to make fundus image pick-up means double as focus target detection means as in the present embodiment; however, focus target detection means intended only for the purpose may be provided separately.

On an optical path between the objective lens 25 and the aperture mirror 22 (the diaphragm 31), a movable diachronic mirror 24 is arranged as an optical path dividing member. Further, on an optical path between the diachronic mirror 24 and the aperture mirror 22 (the diaphragm 31), a movable parallel glass plate 23 is arranged as a member for correcting a deviation of an optical axis caused by the diachronic mirror 24. The diachronic mirror 24 has a wavelength-selecting property of reflecting light within an infrared wavelength range of approximately 900 nm or more including light from an infrared illumination light source 58 for anterior-segment observation and that from the alignment target projection optical system 50 to be described later, and transmitting light within an infrared wavelength range of approximately 900 nm or less including light from the illumination optical system for fundus observation and that from the focus target projection optical system 40 to be described later. The glass plate 23 has approximately the same thickness and refractive index as the diachronic mirror 24. Further, the diachronic mirror 24 is arranged to have an angle of inclination of $\theta$ with respect to the optical axis L1, and the glass plate 23 is arranged to have an angle of inclination of 180° minus $\theta$ with respect to the optical axis L1. At the time of photographing, the diachronic mirror 24 and the glass plate 23 are flipped up synchronously by an inserting/removing mechanism 66 to be removed from the optical path. Besides, a known mechanism such as a solenoid and cam (or motor and the like) may be used for the inserting/removing mechanism 66.

<Focus Target Projection Optical System 40>

Infrared target light emitted from an infrared light source 41 such as an infrared light-emitting diode which emits infrared light having a center wavelength of approximately 880 nm passes through a slit target plate 42 and two deflection-angle prisms 43 attached to the target plate 42, is reflected by the half mirror 44, and further passes through the relay lens 21 to the objective lens 25 to be projected onto the fundus Ef (i.e., focus targets are projected thereto). The light source 41 and the target plate 42 are moved in synchronization with the focusing lens 32 in the optical axis direction by the moving mechanism 39.

<Alignment Target Projection Optical System 50>

The alignment target projection optical system 50 includes two first projection optical systems in a pair having optical axes arranged laterally symmetrical with respect to the optical axis L1, and two second projection optical systems in a pair having optical axes arranged laterally symmetrical with respect to the optical axis L1 forming an angle smaller than the optical axes of the first projection optical systems. The first projection optical systems in a pair include infrared light sources 51 such as infrared light-emitting diodes which emit infrared light having a center wavelength of approximately 940 nm and collimating lenses 52, respectively, and project infrared target light at an infinite distance onto the eye E with approximately parallel light (i.e., alignment targets are projected thereto). On the other hand, the second projection optical systems in a pair include infrared light sources 53 such as infrared light-emitting diodes which emit infrared light having a center wavelength of approximately 940 nm, and projects infrared target light at a finite distance onto the eye E with divergent light (i.e., alignment targets are projected thereto). Besides, in FIG. 2 which is a side view showing the optical system, the alignment target projection optical system 50 is illustrated as arranged in the up-and-down direction; however it is actually arranged in the right-and-left direction.

Figure 3:
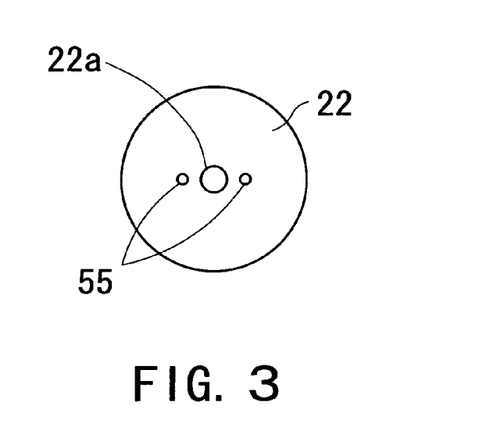
FIG. 3 is a view showing a configuration for forming working dots.

Further, as shown in FIG. 3, around the aperture 22a in the aperture mirror 22, two infrared light sources 55 which emit infrared target light having a center wavelength of approximately 880 nm for forming working dots are arranged laterally symmetrical with respect to the optical axis L1. Incidentally, the light sources 55 may also be configured by arranging an end face of an optical fiber in the vicinity of the aperture mirror 22 and directing infrared light to the optical fiber. In addition, the light sources 55 are arranged in such a manner that their conjugate position is at a distance corresponding to a half of a corneal radius of curvature of the eye E when a working distance between the eye E and the objective lens 25 becomes proper.

<Anterior-Segment Observation Optical System 60>

Infrared illumination light emitted from the infrared illumination light source 58 for anterior-segment observation such as an infrared light-emitting diode is reflected by an anterior-segment of the eye E and the diachronic mirror 24, passes through a field lens 61, a total reflection mirror 62, a diaphragm 63 and a relay lens 64, and is photo-received on a CCD camera 65 for anterior-segment observation having sensitivity to the infrared wavelength range to form an image of the anterior-segment of the eye E. Besides, the light source 58 emits infrared light having a center wavelength of approximately 940 nm. Further, the CCD camera 65 doubles as image-pickup means for alignment target detection (i.e., the anterior-segment observation optical system 60 doubles as an alignment target detection optical system), and picks up the image of the anterior-segment of the eye E formed by the light source 58 and images of the alignment targets formed by the alignment target projection optical system 50. Besides, it is advantageous to make anterior-segment image pick-up means double as alignment target detection means as in the present embodiment; however, alignment target detection means intended only for the purpose may be provided separately.

<Fixation Target Presenting Optical System 70>

Red fixation target light emitted from a fixation target light source (a fixation lamp) 74 such as a red light-emitting diode passes through an aperture in a shielding plate 71 of a rotary disk 72 and a relay lens 75 to be transmitted through the diachronic mirror 37. A part of the red fixation target light transmitted through the diachronic mirror 37 is reflected by the diachronic mirror 34 and passes through the image forming lens 33 to the objective lens 25 to be projected onto the fundus Ef (i.e., a fixation target is projected thereto). The disk 72 is provided with eight shielding plates 71, and the aperture in each shielding plate 71 is either for guiding a visual line so that the vicinity of a posterior pole of the fundus of a right eye comes to a center of photographing, for guiding the visual line so that the vicinity of a posterior pole of the fundus of a left eye comes to the center of photographing, or for guiding the visual line so that a periphery of the fundus is photographed. The disk 72 is rotated by a pulse motor 73, and one of the eight shielding plates 71 is selectively arranged in front of the light source 74. Incidentally, the number of shielding plates 71 is not limited to eight.

Figure 4A:
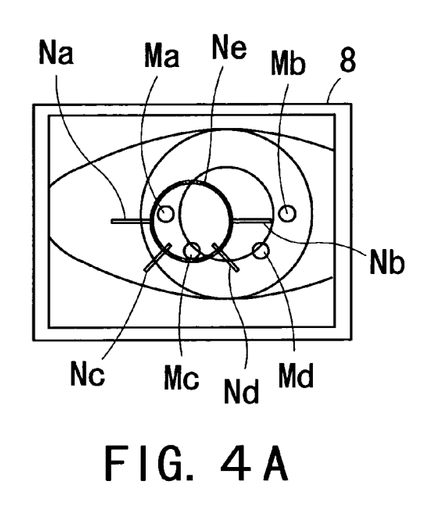
FIG. 4 is a view showing an example of an observation image of an anterior-segment of an eye.
Figure 4B:
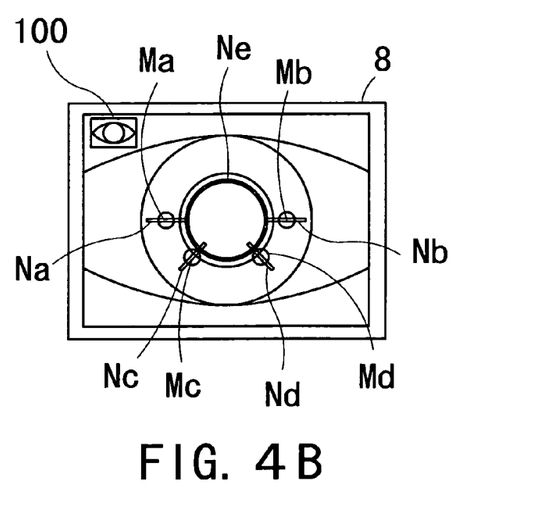

At the time of anterior-segment observation and alignment, the diachronic mirror 24 and the glass plate 23 are inserted in the optical path of the fundus observation/photographing optical system 30 (i.e., the optical path between the objective lens 25 and the aperture mirror 22). The anterior-segment image formed by the light source 58 and the alignment target images formed by the alignment target projection optical system 50 are reflected by the diachronic mirror 24 and picked up by the CCD camera 65. FIGS. 4A and 4B show the anterior-segment image and the alignment target images picked up by the CCD camera 65 and displayed on the monitor 8. Target images Ma and Mb are the alignment target images at an infinite distance formed by the first projection optical systems, and target images Mc an Mad are the alignment target images at a finite distance formed by the second projection optical systems. The second projection optical systems are arranged so that the target images Mc and Md are formed below the target images Ma and Mb.

Figure 6:
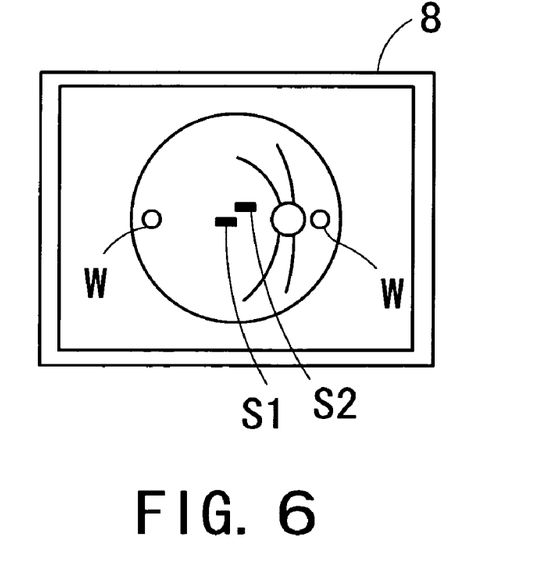
FIG. 6 is a view showing an example of an observation image of a fundus.

Also at the time of fundus observation and focusing, the diachronic mirror 24 and the glass plate 23 are inserted in the optical path of the fundus observation/photographing optical system 30. The fundus image formed by the illumination optical system for fundus observation and the focus target images formed by the focus target projection optical system 40 are transmitted through the diachronic mirror 24 and the glass plate 23 to be picked up by the CCD camera 38. FIG. 6 is a view showing the fundus image and the focus target images picked up by the CCD camera 38 and displayed on the monitor 8. Target images S1 and S2 are the focus target images formed by the focus target projection optical system 40.

At the time of photographing, the diachronic mirror 24 and the glass plate 23 are removed from the optical path by the inserting/removing mechanism 66. The image of the fundus Ef is picked up by the CCD camera 35 via the objective lens 25 to the diachronic mirror 34. Besides, such a constitution may be employed that the CCD camera 35 for photographing doubles as the camera for fundus observation.

Respective image signals outputted from the CCD cameras 65, 38 and 35 are inputted to an image processing part 80. The image processing part 80 detects the alignment target images based on the image signal from the CCD camera 65 and the focus target images based on the image signal from the CCD camera 38. Further, the image processing part 80 is connected to the monitor 8 to control images displayed thereon. The control part 81 is connected with the image processing part 80, the Y-moving unit 6, the X- and Z-moving unit 7, the joystick 4, the moving mechanism 39, the inserting/removing mechanism 66, the pulse motor 73, a photographing switch 83, a switch part 84 having various switches, the light sources, and the like. (In FIG. 2, a part of connection lines are not illustrated.)

In the switch part 84, a switch 84a is for selecting (switching) between a manual alignment mode where the examiner operates the joystick 4 to perform alignment of the photographing part 3 with the eye E and an automatic alignment mode where driving of the X- and Z-moving unit 7 and the Y-moving unit 6 are controlled by the control part 81 based on alignment information detected by the image processing part 80 to perform alignment of the photographing part 3 with the eye E. A switch 84b is for selecting (switching) between an automatic display-switching mode where display on the monitor 8 is automatically switched from the anterior-segment image to the fundus image and a manual display-switching mode where the examiner performs the switching through switch operation. A switch 84c is for switching display on the monitor 8 from the fundus image to the anterior-segment image in the automatic display-switching mode and the manual display-switching mode. A switch 84d is for switching display on the monitor 8 from the anterior-segment image to the fundus image in the manual display-switching mode.

Hereinafter, an operation of the apparatus having the above-described configuration will be described. Firstly described will be the operation in the manual alignment mode where the examiner operates the joystick 4 to perform alignment of the photographing part 3 with the eye E. In this case, the manual alignment mode is previously selected by the switch 84a.

First, the face of the examinee is supported by the face supporting unit 5. Then, the examinee is instructed to fixate the fixation target. Here, a right eye is to be photographed. In the initial stage, the diachronic mirror 24 and the glass plate 23 are inserted into the optical path of the fundus observation/photographing optical system 30, and the anterior-segment image picked up by the CCD camera 65 is displayed on the monitor 8. While observing the anterior-segment image displayed on the monitor 8, the examiner moves the photographing part 3 in the X- and Y-directions so that the anterior-segment image is placed in the center of a screen on the monitor 8. In addition, the examiner moves the photographing part 3 in the Z-direction to bring the anterior-segment image into focus. When the anterior-segment image comes to be placed in the center of the screen on the monitor 8, the four target images Ma, Mb, Mc and Md also come to be displayed (appear) as shown in FIG. 4A. In FIG. 4A, reference letters Na, Nb, Nc and Nd indicate reticule marks respectively in a line shape, and a reference letter Ne indicates a ring mark showing a pupil diameter necessary for the photographing, all of which are electrically formed by the image processing part 80. In the alignment, the photographing part 3 is moved in the X- and Y-directions so that the target images Ma, Mb, Mc and Md are respectively placed on the reticule marks Na, Nb, Nc and Nd as shown in FIG. 4B. Further, the photographing part 3 is moved in the Z-direction to bring the target images Ma to Md into focus.

Figure 5:
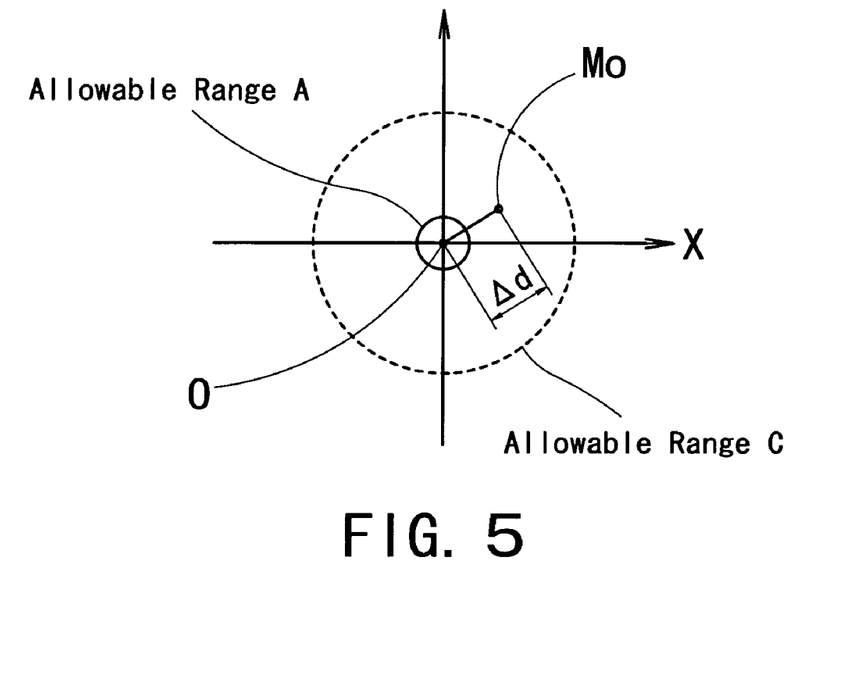
FIG. 5 is a view showing an example of a reference condition for alignment with an eye.

When the target images Ma to Md picked up by the CCD camera 65 are detected by the image processing part 80, the control part 81 obtains information on an alignment state in the X-, Y- and Z-directions based on the target images Ma to Md. That is to say, the control part 81 obtains, as shown in FIG. 5, a deviation (shift) amount Δd with reference to an alignment reference position O in the X- and Y-directions while defining the midpoint between the target images Ma and Mb as a corneal vertex position Mo. Then, the control part 81 nudges appropriateness of the alignment state in the X- and Y-directions (i.e., alignment completion) based on whether the deviation amount Δd stably falls within a predetermined first allowable range A of alignment completion for a predetermined time (for example, 10 frames of image processing, 0.3 second, or the like) (i.e., whether a first reference condition for alignment is satisfied). Further, the alignment state in the Z-direction is detected by comparing a distance between the target images Ma and Mb with a distance between the target images Mc and Md. It utilizes a characteristic that in the case of forming corneal reflexes using light sources at an infinite distance and light sources at a finite distance, respectively, a height of corneal reflexes formed by the light sources at an infinite distance is not changed even when the working distance is changed while a height of corneal reflexes formed by the light sources at a finite distance is changed as a working distance is changed (for details, see U.S. Pat. No. 5,463,430 corresponding to Japanese Patent Application Unexamined Publication No. Hei6-46999). The control part 81 obtains a deviation (shift) amount with respect to an alignment reference position in the Z-direction, and judges appropriateness of the alignment state in the Z-direction (i.e., alignment completion) based on whether the deviation amount stably falls within a predetermined first allowable range of alignment completion for a predetermined time (i.e., whether a first reference condition for alignment is satisfied).

If the alignment state in the X-, Y- and Z-directions satisfies the first reference condition, display switching from the anterior-segment image to the fundus image is allowed. Here, if the manual display-switching mode is selected by the switch 84b, a mark 100 for informing the alignment completion blinks on the monitor 8. Through a display of the mark 100, the examiner may be informed that the alignment is proper. Then, the examiner presses the switch 84d to make the display switching from the anterior-segment image to the fundus image. When the switch 84d is pressed, the fundus image picked up by the CCD camera 38 is displayed on the monitor 8.

On the other hand, if the automatic display-switching mode is selected by the switch 84b, the control part 81 controls to make the display switching from the anterior-segment image to the fundus image automatically in accordance with the judgment of the alignment completion in the X-, Y- and Z-directions.

When the alignment state is made proper to some extent, two working dots W formed by the light sources 55 come to be displayed (appear) as shown in FIG. 6. The examiner checks the focus of the working dots W, a flare in the fundus image, and the like while observing the fundus image, and further performs alignment through operation of the joystick 4 so that the photographing may be performed in a desired state.

After the alignment is performed while the fundus image is observed, the target images S1 and S2 are displayed (appear) in the center as shown in FIG. 6. Therefore, the light source 41, the target plate 42 and the focusing lens 32 are moved in the optical axis direction based on the target images S1 and S2 to perform focusing on the fundus Ef. If the fundus Ef is not brought into focus, the target images S1 and S2 are displayed (appear) separately, and if the fundus Ef is brought into focus, they are displayed (appear) in coincident with each other. While the focusing can be performed manually, the present apparatus is provided with an automatic focusing mechanism. In automatic focusing, the target images S1 and S2 are detected and processed by the image processing part 80, and their separation information is transferred to the control part 81. Based on the separation information on the target images S1 and S2, the control part 81 performs focusing on the fundus Ef by driving and controlling the movement mechanism 39 so that both the images coincide with each other.

In the switch part 84, a switch 84e is for selecting (switching) whether or not to perform the automatic focusing. A switch 84f is for actuating the automatic focusing. A switch (dial) 84g is for performing manual focusing.

In the automatic focusing on the fundus Ef, errors are sometimes produced due to various causes such as blink, unstable fixation and a small pupil. While the automatic focusing is performed after the display on the monitor 8 is switched from the anterior-segment image to the fundus image, the causes of the errors are hard to grasp in such a state. For this reason, when the automatic focusing is actuated by the switch 84f (i.e., when a signal from the switch 84f is inputted), the control part 81 controls to switch the display on the monitor 8 from the fundus image to the anterior-segment image. Accordingly, the state of the eye can be easily observed and checked, allowing an easier grasp of the causes of the errors.

Upon completion of the focusing, the examiner presses the photographing switch 83 to perform the photographing. When a trigger signal from the switch 83 is inputted, the control part 81 drives and controls the inserting/removing mechanism 66 to remove the diachronic mirror 24 and the glass plate 23 from the optical path, and have the light source 14 emit light. By the emission from the light source 14, the fundus Ef is illuminated with the visible light, and the light reflected from the fundus Ef is photo-received on the CCD camera 35 to form the image of the fundus Ef. Further, on the monitor 8, the fundus image picked up by the CCD camera 35 is displayed in color. In addition, the fundus image (photographed image) is stored in an image memory included in the image processing part 80.

Next, an operation in a case where the automatic alignment mode is set by the switch 84a will be described. In this case, the automatic alignment mode is previously selected by the switch 84a.

The examiner performs rough alignment of the photographing part 3 with the eye E through operation of the joystick 4 while observing the anterior-segment image displayed on the monitor 8. When the target images Ma to Md picked up by the CCD camera 65 are detected by the image processing part 80, the control part 81 obtains the information on the alignment state in the X-, Y- and Z-directions based on the target images Ma to Md, and drives and controls the X- and Z-moving unit 7 and the Y-moving unit 6 to perform the automatic alignment so as to satisfy the first reference condition. Then, when the alignment is completed, the control part 81 stops the automatic alignment. Thereafter, as in the case of the manual alignment mode, the control part 81 controls to make the display switching from the anterior-segment image to the fundus image based on the setting of whether the display switching is made automatically or manually.

Here, in the automatic alignment mode, another judgment condition for starting re-implementation of the automatic alignment is included, in contrast to the manual alignment mode. The control part 81 makes judgment based on whether or not the deviation amount $\Delta d$ in the X- and Y-directions falls within a predetermined second allowable range C of alignment which is set greater than the first allowable range A (i.e., whether or not a second reference condition for alignment is satisfied). Same shall apply to the deviation amount in the Z-direction. That is to say, the control part 81 stops the automatic alignment until the deviation amount $\Delta d$ goes out of the second allowable range C, and re-implements the automatic alignment when the deviation amount $\Delta d$ goes out of the second allowable range C. The second allowable range C in the X- and Y-directions is, for example, a range of ±1.5 mm with respect to the alignment reference position O.

As mentioned above, by stopping the automatic alignment after the completion of the alignment, the examiner may perform fine adjustment of a photographing position through operation of the joystick 4 while observing the fundus image displayed on the monitor 8. When the display switching is made from the anterior-segment image to the fundus image, the two working dots W formed by the light sources 55 are displayed (appear) as shown in FIG. 6. While observing the fundus image, the examiner checks the focus of the working dots W, the flare in the fundus image and the like, and further performs the alignment through operation of the joystick 4 so that the photographing may be performed in a desired state. In the automatic alignment utilizing the anterior-segment image, there is a case where a flare slightly appears in the fundus image due to individuality in a cornea and a crystalline lens; however, as the manual alignment can be performed so as to avoid the flare, unfavorable photographing can be prevented. Further, when the alignment state comes not to satisfy the second reference condition, the automatic alignment is performed while displaying the fundus image (observation image), so that a burden of the manual alignment is reduced and the alignment may be performed easily.

In addition, when the alignment is judged as completed, the automatic focusing is implemented. Upon completion of the alignment and the focusing, the photographing switch 83 is pressed to implement the photographing.

Here, in the case of the automatic alignment mode and the automatic display-switching mode, even in the eye of which fixation is unstable, when the fixation is temporarily stabilized and the alignment completion is judged, the display on the monitor 8 is switched from the anterior-segment image to the fundus image and the automatic alignment is stopped. However, when the fixation becomes unstable again after a while, the fundus image displayed on the monitor 8 also becomes unstable. Then, when the alignment state comes not to satisfy the second reference condition, the automatic alignment is performed again. In such a case, for making a check of stability of the fixation of the eye and the like, it is effective to once return to the anterior-segment image which is easier to observe and check than the fundus image.

When the switch 8c is pressed in a state where the automatic alignment mode is selected and the fundus image is displayed on the monitor 8 in either of the manual display-switching and the automatic display-switching modes, the control part 81 controls to switch the display on the monitor 8 from the fundus image to the anterior-segment image and stop (prohibit) the automatic alignment. The display of the anterior-segment image and the stop of the automatic alignment are continued while the switch 84c is pressed, i.e., while the signal from the switch 84c is inputted. Then, when the signal from the switch 84c comes not to be inputted, the control part 81 controls to cancel the stop of the automatic alignment (permit the automatic alignment) and allows the display on the monitor 8 to switch from the anterior-segment image to the fundus image.

As mentioned above, through operation of the switch 84c, the display on the monitor 8 is switched from the fundus image to the anterior-segment image and the automatic alignment is stopped; therefore, through observation of the anterior-segment image, it becomes easier for the examiner to check the stability of the fixation of the eye. If the eye frequently moves, remedies such as calling attention to the examinee are applied. Then, if the stabilization of the fixation of the eye is confirmed through observation of the anterior-segment image, the stop of the automatic alignment is canceled, and the display on the monitor 8 is allowed to switch from the anterior-segment image to the fundus image. Then, if the alignment state comes to satisfy the first reference condition, the display on the monitor 8 is switched from the anterior-segment image to the fundus image. Consequently, fine adjustment of the alignment can be performed through operation of the joystick 4 while the fundus image is observed under a state where the fixation of the eye is relatively stable.

As mentioned above, only through operation of the switch 84c, the display switching from the fundus image to the anterior-segment image and the temporary stop of the automatic alignment can be made, so that a check of the stability of the fixation can also be easily made with simple operation while effectively utilizing the function of the automatic alignment.

Incidentally, while the display switching from the fundus image to the anterior-segment image and the temporary stop of the automatic alignment are continued while the signal from the switch 84c is inputted in the above description, it is also preferable to provide and operate a switch for allowing the display on the monitor 8 to switch from the anterior-segment image to the fundus image and canceling the temporary stop of the automatic alignment.

Incidentally, as to the display switching between the anterior-segment image and the fundus image, such a constitution may also be included that when switched to a state of anterior-segment observation, the anterior-segment image is largely displayed and the fundus image is displayed in a small window synthetically, and when switched to a state of fundus observation, the fundus image is largely displayed and the anterior-segment image is displayed in the small window synthetically.

Figure 7:
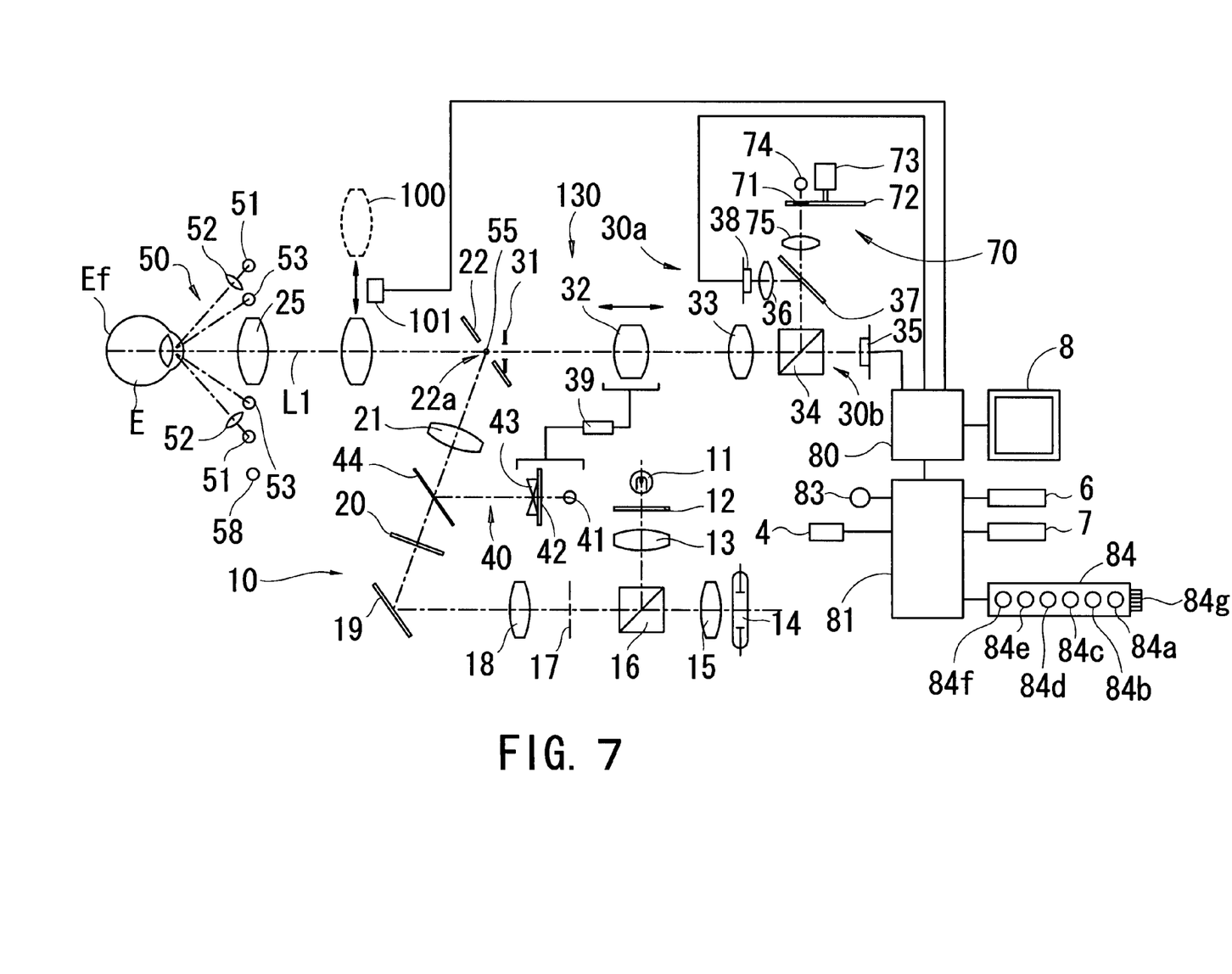
FIG. 7 is a view showing a schematic configuration of an optical system and a control system in a modified embodiment of the fundus camera.

Next, a modified example of the present invention will be described. FIG. 7 is a view showing a schematic configuration of an optical system and a control system in the modified example. In FIG. 7, constituting members assigned the same reference numerals as in FIG. 2 represent the same and description thereof is omitted unless specific description is given.

In contrast to the optical system in FIG. 2, an anterior-segment and fundus observation/photographing optical system 130 is provided with an insert able and removable lens 100 in the optical path between the objective lens 25 and the aperture mirror 22, and the CCD camera 38 doubles as image-pickup means for anterior-segment observation and image-pickup means for fundus observation. The lens 100 is inserted and removed by a moving device 101. When the lens 100 is inserted in the optical path, the anterior-segment image is picked up by the CCD camera 38, and when the lens 100 is removed from the optical path, the fundus image is picked up by the CCD camera 38.

In addition, in the apparatus in this modified example, when the automatic alignment mode is selected and the lens 100 is inserted in the optical path, the automatic alignment is performed based on the alignment target images projected by the alignment target projection optical system 50. When the alignment state comes to satisfy the first reference condition, the lens 100 is automatically removed from the optical path, and the display on the monitor 8 is switched from the anterior-segment image to the fundus image. Consequently, the automatic alignment based on the alignment target images is stopped, allowing fine adjustment of the alignment to be performed through operation of the joystick 4 while the fundus image is observed. When the switch 84c is pressed as in the previous example under the state where the display on the monitor 8 is the fundus image, the lens 100 is inserted into the optical path to switch the display on the monitor 8 from the fundus image to the anterior-segment image and the automatic alignment is temporarily stopped.

Incidentally, the present invention may be applied also to an apparatus with a constitution where the second automatic alignment is performed based on the working dots formed by the light sources 55 at the time of the fundus observation (when the lens 100 is removed). Specifically, such a constitution is considered that the second automatic alignment is implemented at the time when the fixation of the eye is stabilized and the display on the monitor 8 is switched from the anterior-segment image to the fundus image.

The foregoing description of the preferred embodiments of the invention has been presented for purposes of illustration and description. It is not intended to be exhaustive or to limit the invention to the precise form disclosed, and modifications and variations are possible in the light of the above teachings or may be acquired from practice of the invention. The embodiments chosen and described in order to explain the principles of the invention and its practical application to enable one skilled in the art to utilize the invention in various embodiments and with various modifications as are suited to the particular use contemplated. It is intended that the scope of the invention be defined by the claims appended hereto, and their equivalents.

What is claimed is:

1. A fundus camera for photographing a fundus of an eye of an examinee, the fundus camera comprising:
   a photographing part in which a fundus photographing optical system is arranged;
   a moving unit which moves the photographing part;
   a fundus observation optical system having a first image-pickup element which picks up an image of the fundus;
   an anterior-segment observation optical system having a second image-pickup element which picks up an image of an anterior-segment of the eye;
   a display unit capable of displaying the fundus image picked up by the first image-pickup element and the anterior-segment image picked up by the second image-pickup element;
   a control part which obtains information on alignment of the photographing part with the eye and drives the moving unit based on the obtained alignment information so that an alignment state of the photographing part with the eye satisfies a first reference condition, stops the driving of the moving unit when the alignment state satisfies the first reference condition while allowing a display on the display unit to switch from the anterior-segment image to the fundus image and, drives the moving unit again based on the alignment information when the alignment state subsequently fails to satisfy a second reference condition which is set greater than the first reference condition; and
   a first input switch for inputting a signal for switching a display on the display unit from the fundus image to the anterior-segment image,
   wherein the control part prohibits the driving of the moving unit when the signal from the first input switch is input after the display is switched from the image of the anterior-segment to the fundus image, even if the alignment state fails to satisfy the second reference condition.

2. The fundus camera according to claim 1, wherein the control part prohibits the driving of the moving unit while the signal from the first input switch is inputted, and permits the driving of the moving unit when the input of the signal from the first input switch is stopped.

3. The fundus camera according to claim 1, further comprising a second input switch for inputting a signal for allowing the display on the display unit to switch from the anterior-segment image to the fundus image,
   wherein the control part permits the driving of the moving unit when the signal from the second input switch is inputted.

4. The fundus camera according to claim 1, further comprising an alignment mode selecting switch for selecting a mode for alignment of the photographing part with the eye from among a manual alignment mode and an automatic alignment mode.

5. The fundus camera according to claim 1, further comprising an alignment target projection optical system which projects an alignment target onto the anterior segment, wherein the second image-pickup element picks up an image of the alignment target formed on the anterior-segment, and the control part obtains the alignment information of the photographing part with the eye based on an output from the second image-pickup element.

6. The fundus camera according to claim 1, wherein the fundus photographing optical system includes a focusing lens movable in a direction of an optical axis thereof, and the control part obtains focus information on the fundus, controls movement of the focusing lens based on the obtained focus information so that a focus state on the fundus satisfies a predetermined coincidence condition, and controls the display unit to display the anterior-segment image during the control of the movement of the focusing lens.

7. The fundus camera according to claim 6, further comprising a focus target projection optical system which projects a focus target onto the fundus, wherein the first image-pickup element picks up an image of the focus target formed on the fundus, and the control part obtains the focus information on the fundus based on an output from the first image-pickup element.

8. The fundus camera according to claim 1, wherein the first image-pickup element is used as the second image-pickup element.

9. The fundus camera according to claim 1, further comprising a display-switching mode selecting switch for selecting a mode for switching the display from the anterior-segment image to the fundus image from among a manual display-switching mode and an automatic display-switching mode.

10. The fundus camera according to claim 1, wherein the control part drives the moving unit again so that the alignment state satisfies the first reference condition again when the alignment state comes not to satisfy the second reference condition, and prohibits the driving of the moving unit when the signal from the first input switch is inputted after the display is switched from the anterior-segment image to the fundus image even if the alignment state does not satisfy the first reference condition.

* * * * *